US007897646B2

(12) United States Patent
Bauer et al.

(10) Patent No.: US 7,897,646 B2
(45) Date of Patent: Mar. 1, 2011

(54) USE FOR BUDESONIDE AND FORMOTEROL

(75) Inventors: Carl-Axel Bauer, Lund (SE); Jan Trofast, Lund (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 10/010,283

(22) Filed: Nov. 13, 2001

(65) Prior Publication Data

US 2002/0042404 A1 Apr. 11, 2002
US 2006/0189587 A9 Aug. 24, 2006

Related U.S. Application Data

(63) Continuation of application No. 09/670,457, filed on Sep. 26, 2000, now abandoned, which is a continuation of application No. 09/194,290, filed as application No. PCT/SE98/01599 on Sep. 9, 1998, now abandoned.

(30) Foreign Application Priority Data

Sep. 19, 1997 (SE) .................................... 9703407-8

(51) Int. Cl.
A61K 31/56 (2006.01)
A61K 31/16 (2006.01)
A61K 9/12 (2006.01)

(52) U.S. Cl. ........................... 514/630; 514/171; 424/45

(58) Field of Classification Search ................. 514/630, 514/171; 424/45
See application file for complete search history.

(56) References Cited

U.S. PATENT DOCUMENTS

| 5,250,286 | A |   | 10/1993 | Skupin |  |
|---|---|---|---|---|---|
| 5,674,860 | A | * | 10/1997 | Carling et al. | 514/171 |
| 5,684,199 | A |   | 11/1997 | Francotte |  |
| 5,795,564 | A |   | 8/1998 | Aberg et al. |  |
| 5,972,919 | A | * | 10/1999 | Carling et al. | 514/171 |
| 5,996,576 | A |   | 12/1999 | Yule |  |
| 6,030,604 | A | * | 2/2000 | Trofast | 424/46 |
| 6,277,862 | B1 | * | 8/2001 | Giardina et al. | 514/311 |
| 6,598,603 | B1 | * | 7/2003 | Andersson et al. | 128/200.24 |

FOREIGN PATENT DOCUMENTS

| CA | 2123909 | 6/1993 |
|---|---|---|
| CA | 2356145 | 6/1993 |
| EP | 0 416 950 A1 | 3/1991 |
| EP | 0 416 951 A1 | 3/1991 |
| EP | 0 523 638 | 1/1993 |
| EP | 1085877 | 12/1999 |
| EP | 1 014 993 | 7/2000 |
| EP | 0613371 | 3/2002 |
| SE | 9703407-8 | 9/1998 |
| WO | WO 92/11280 | 7/1992 |
| WO | WO 97/11783 | 4/1997 |
| WO | WO 98/15280 | 4/1998 |
| WO | WO 98/31351 | 7/1998 |
| WO | WO 99/00134 | 1/1999 |
| WO | WO 99/64014 | 12/1999 |
| WO | WO 00/30608 | 6/2000 |
| WO | WO 00/35441 | 6/2000 |
| WO | WO 00/53188 | 9/2000 |

OTHER PUBLICATIONS

Cazzola et al. "Effect of salmeterol and formoterol in patients with chronic obsructive pulmonary disease" Pulmonary Pharmacology 1994, 7/2 p. 103-107.*
Nederlands Tijdschrift voor Geneeskunde "Opportunistic lung infection in patients with chronic obstructive pulmonary disease" 1996 140/2 pp. 94-98 ISSN: 0028-2162 CODEN:NETJAN.*
Saunders Manual of Medicine Practice. Rakel 1996.*
Renkema et al. "Effects of long-term treatment with corticosteroids in COPD." Chest, 1996, vol. 109, No. 5. abstract AN 1996:325104.*
The Merck Manual, sixteenth Edition, 1992, pp. 658-659.*
Opportunistic Lung Infections in Patients with Chronic Obstructive Pulmonary Disease- A Side Effect of Inhalation Corticosteroids? Smeenk et al. Nederlands Tijdschrift Geneeskunde vol. 13, Jan. Issue 140 (2) 1996 pp. 94-98. Full English translation.*
Barnes et al., "Chronic obstructive pulmonary disease: molecular and cellular mechanisms," Eur. Respir. J. 22:672-688 (2003).
Buist, "Definitions," in Asthma and Chronic Obstructive Pulmonary Disease, Barnes et al. eds., Acad. Press, pp. 3-6 (2002).
Calverley et al., "Maintenance therapy with budesonide and formoterol in chronic obstructive pulmonary disease," Eur. Respir. J. 22:912-919 (2003).
Rabe, "Combination therapy for chronic obstructive pulmonary disease; one size fits all?" Eur. Respir. J. 22:874-875 (2003).
"Analysis of DIN-LINK Co-prescription Records for Inhaled Steroids and Long-Acting Beta Agonists in the Period 1990-1998" pp. 1-2, appendices A and B; published 1990-1998.
Pearson et al., "British Thoracic Society Guidelines for Treatment of COPD" Thorax 52 (Suppl. 5):S1-S28 (1997).
Jackevicius et al., "Prehospitalization Inhaled Cortiscoteroid Use in Patients With COPD or Asthma" Chest 111:296-302 (1997).
"Foradil" MIMS-Monthly Index of Medical Specialties Jan. 10 (1996).
Pauwels, "COPD: The Scope of the Problem in Europe" Chest 117:332D-335S (2000).
Roberts et al., "Which patients are prescribed inhaled anti-asthma drugs?" Thorax 49(11):1090-1095 (1994).
Van Andel et al., "Analysis of Inhaled Corticosteroid and Oral Theophylline Use Among Patients With Stable COPD from 1987 to 1995" Chest 115:703-707 (1999). Compendium Suisse des Medicaments, 15 th Ed. 1997/1998, Ed. Grand Public, compiled Jun. 1996, pp. 2-3,419-420,866 (in French).
Compendium Suisse des Medicaments, 18th Ed. 1997, compiled Jun. 1996, pp. 5,849-851 and 1635-1636 (in French).
"American Thoracic Society: Standards for the Diagnosis and Care of Patients with Chronic Obstructive Pulmonary Disease," Am. J. Respir. Care Med. 152:S77-S121 (1995).
"Atemstillstand" Pschyrembel Klinisches Wörterbuch (2002) (in German).
Auffarth et al., "Effects of inhaled budesonide on spirometric values, reversibility, airway responsiveness, and cough threshold in smokers with chronic obstructive lung disease" Thorax 46:372-377 (1991).
Barnes, "Inhaled steroids in COPD" The Lancet 351:766-767 (1998).
Basic Reference Manual, vol. 1, revised ed. of 1988, issued by IMS International.

(Continued)

Primary Examiner — Jennifer Kim
(74) Attorney, Agent, or Firm — Fish & Richardson P.C.

(57) ABSTRACT

The invention provides the use of formoterol and budesonide in the treatment of chronic obstructive pulmonary disease.

85 Claims, No Drawings

OTHER PUBLICATIONS

"Bronchodilators and anti-inflammatories," *Monthly Index of Medical Specialities (MIMS)* 242-256 (Sep. 1997).
Boyd et al., "An Evaluation of Salmeterol in the Treatment of Chronic Obstructive Pulmonary Disease (COPD)," *Eur. Resp. J.* 10:815-821 (1997).
Burge et al. "Randomised, double blind, placebo controlled study of fluticasone propionate in patents with moderate to severe chronic obstructive pulmonary disease: the ISOLDE trial," *British Med. J.* 320:1297-1303 (2000).
Davies et al., "Oral corticosteroid trials in the management of stable chronic obstructive pulmonary disease," *Q. J. Med.* 92:395-400 (1999).
"Disorders of the Airways," *Current Medical Diagnosis and Treatment 1997* 36th ed. pp. 241-255, Stamford, CT: Appleton and Lange (1997).
Dompeling et al., "Slowing the deterioration of Asthma and Chronic Obstructive Pulmonary Disease Observed during Bronchodilator Therapy by Adding Inhaled Corticosteroids," *Ann. Intern. Med.* 118(10):770-778 (1993).
Engel et al., "A trial of inhaled budesonide on airway responsiveness in smokers with chronic bronchitis" *Eur. Respir. J.* 2:935-939 (1989).
Fabbri et al., "Global Strategy for the Diagnosis, Management and Prevention of COPD: 2003 update" *Eur. Respir. J.* 22:1-2 (2003).
Flenley, "Chronic Obstructive Pulmonary Disease," *Disease-A-Month* 34:549-599 (1988).
"Foradil" *Compendium Suisse des Medicaments*, Supplement 1a pp. 7-8 (1991) (in French).
"Foradil," *Compendium Suisse des Medicaments*, 15th Ed. 1997/1998, Ed. Grand Public, compiled Jun. 1996, pp. 419-420, 866 (in French).
"Foradil," *Compendium Suisse des Medicaments*, 18th Ed. 1997, compiled Jun. 1996, pp. 849-850 and 1635 (in French).
"Foradil," Patient information leaflet, published by IKS, Switzerland (Dec. 1990) (in French).
Gibson et al., *Respiratory Medicine* Table of contents (2002).
"GOLD: Global Initiative for Chronic Obstructive Lung Disease," Executive Summary; National Institutes of Health, National Heart Lung and Blood Institute, NIH Publication No. 2701A, pp. 1-30 (Mar. 2001).
"GOLD: Global Initiative for Chronic Obstructive Lung Disease; Global Strategy for the Diagnosis, Management, and Prevention of Chronic Obstructive Pulmonary Disease," based on Apr. 1998 NHLBI/WHO Workshop, pp. 1-100 (2004 Update).
Jeffery "Structural and inflammatory changes in COPD: a comparison with asthma" *Thorax* 53:129-136 (1998).
Keatings et al., "Effects of Inhaled and Oral Glucocorticoids on Inflammatory Indices in Asthma and COPD" *Am. J. Respic. Crit. Care Med.* 155:542-548 (1997).
Kerstjens et al., "A Comparison of Bronchodilator Therapy with or without Inhaled Corticosteroid Therapy for Obstructive Airway Disease," *New Eng. J. Med.* 327:1413-1419 (1992).
Leff et al., "Theraputic Regimens in Chronic Obstructive Pulmonary Disease," *Pulmon. Crit. Care Pharmacol. Therapeut.* Ch. 86:837-844 (1996).
Niewoehner et al., "Effect of Systemic Glucocorticoids on Exacerbations of Chronic Obstructive Pulmonary Disease" *New Eng. J. Med.* 340(25):1941-1947 (1999).
Norman, "COPD: New Developments and Therapeutic Opportunities" *Drug News Perpect.* 11(7):431-437 (1988).
Pauwels et al., "Long-Term Treatment with Inhaled Budesonide in Persons with Mild Chronic Obstructive Pulmonary Disease Who Continue Smoking" *N. Eng. J. Med.* 340:1948-1953 (1999).
Postma, "Inhaled therapy in COPD: what are the benefits?" *Respiratory Medicine* 85:447-449 (1991).
"Pulmicort" ABPI Data Sheet Compendium, p. 146-147 (1995/1996).
Schultze-Werninghaus, "Multicenter 1-Year Trial on Formoterol, a New Long-Acting $\beta_2$-Agonist, in Chronic Obstructive Airway Disease," *Lung* Suppl:83-89 (1990).
Siafakas et al., "Optimal Assessment and Management of Chronic Obstructive Pulmonary Disease (COPD)," *Eur. Respir. J.* 8:1398-1420 (1995).
Soriano et al., "Inhaled Corticosteroids with/Without Long-Acting b-Agonists Reduce the Risk of Rehospitalization and Death in COPD Patients," *Am. J. Respir. Medic.* 2:67-74(2003).
Stalenheim et al., "Efficacy and Tolerance of a 12-Week Treatment with Inhaled Formoterol in Patients with Reversible Obstructive Lung Disease," *Respiration* 61:305-309 (1994).
Stedman's Medical Dictionary, 25th ed., Baltimore: Williams and Wilkins; p. 428.
Szafranski et al., "Efficacy and safety of budesonide/formoterol in the management of chronic obstructive pulmonary disease" *Eur. Respir. J.* 21:74-81 (2003).
Trechsel, "Foradil in medical practice; 7 case studies" Ciba Geigy (1992).
Van Schayck et al., "Do patients with COPD benefit from treatment with inhaled corticosteroids?" *Eur. Respir. J.* 9:1969-1972 (1996).
Vestbo et al., "Long-term effect of inhaled budesonide in mild and moderate chronic obstructive pulmonary disease: a randomised controlled trial," *Lancet* 353:1819-1823 (1999).
Watson et al., "Failure of Inhaled Corticosteroids to Modify Bronchoconstrictor or Bronchodilator Responsiveness in Middle-Aged Smokers with Mild Airflow Obstruction" *Chest* 101(2):350-355 (1992).
Weiner et al., "Inhaled Budesonide Therapy for Patients with Stable COPD," *Chest* 108:1568-1571 (1995).
CA 126:259329 Renkema et al.
C. Wyser et al., "Neue Aspekte in der Behandlung des Asthma bronchiale und chronisch obstruktiver Lungenkrankheiten", 1997, Schweiz Med Wochenscher, vol. 127, pp. 885-890.
Jean H. Marsac, Fotis D. Vlastos, and Jacques G. Lacronique "Inhaled beta adrenergic agonists and inhaled steroids in the treatment of asthma" Annals of Allergy Sep. 1989, vol. 63, No. 3, pp. 220-224.
Francis P.V. Maesen, M.D., Ph.D., F.C.C.P. Joseph J. Smeets, Hendrik L. L. Gubbelmans, M.D., and Petra G.M. A. Zweers, M.D. "Formoterol in the Treatment of Nocturnal Asthma" Chest 98 Oct. 4, 1990 pp. 886-870.
Francis P.V. Maesen, M.D., Ph.D., F.C.C.P., Joseph J. Smeets; Hendrik L. L. Gubbelmans, M.D., and Petra G.M. A. Zweers, M.D. "Bronchodilator Effect of Inhaled Formoterol vs. Salbutamol Over 12 Hours" Chest/97/3/Mar. 1990.
Romain A. Pauwels, M.D., Claes-Goran Lofdahl, M.D., Peter J. Barnes, M.D., and Anders Ullman, M.D. "Effect of Inhaled Formoterol and Budesonide on Exacerbations of Asthma" vol. 337 No. 20, Nov. 13, 1997.
Curriculum Vitae of Charles Richard William Beasley.
Statutory Declaration of Charles Richard William Beasley.
New Ethicals Catalogue, Dec. 1990, No. 3 p. 50.
Additive effects of Budesonide and Formoterol in Reducing Severe Asthma Exacerbations Over 12 Months, O'Byrne et al. On behalf of international study group and Astra Draco AB Lung Sweden.
Effect of Inhaled Formoterol and Budesonide on Exacerbations of Asthma, Pauwels et al., Massachusetts Medical Society, Nov. 13, 1997, vol. 337, No. 20, p. 1405.
Response by Astra to EPO, dated Nov. 22, 1995.
Postma et al., "Rationale for the Dutch Hypothesis* Allergy and Airway Hyperresponsiveness as Genetic Factors and Their Interaction With Environment in the Development of Asthma and COPD" *Chest* 126:96S-104S (2004).
Renkema et al., "Effects of Long-term Treatment With Corticosteroids in COPD" *Chest* 109:1156-1162 (1996).
Soriano et al., "The Proportional Venn Diagram of Obstructive Lung Disease* Two Approximations From the United States and the United Kingdom" *Chest* 124:474-481 (2003).
Vestbo et al., "Update on the "Dutch hypothesis" for chronic respiratory disease" *Thorax* 53(Suppl.2):S15-S19 (1998).
Morice et al., "A comparison of nebulized budesonide with oral prednisolone in the treatment of exacerbations of obstructive pulmonary disease", Clinical Pharmacology & Therapeutics vol. 60, pp. 675-678 (1996).
Minutes of the May 6, 2008 oral proceedings before the European Patent Office Technical Board of Appeal in the opposition against EP 1014993 (4 pages).

Written decision of the European Patent Office Technical Board of Appeal in the opposition against EP 1014993, dated May 6, 2008 (17 pages).

Ankerst et al., "Tolerability of a high dose of budesonide/formoterol in a single inhaler in patients with asthma," Pulm Pharmacol Ther., 16:147-51, 2003.

Arvidsson et al., "Inhaled formoterol during one year in asthma: a comparison with salbutamol," Eur Respir J, 4:1168-1173, 1991.

Aubier et al., "Salmeterol/Fluticasone propionate (50/500 µg) in combination in a Diskus® inhaler (Seretide®) is effective and safe in the treatment of steroid-dependent asthma," Respir. Med. 93:876-884, 1999.

Bartow et al., "Formoterol: An Update of its Pharmacological Properties and Therapeutic Efficacy in the Management of Asthma," Drugs, 55(2):303-322, 1998.

Bond, "A strategy that works," New Zealand Medical Journal, p. 369, Aug. 28, 1991.

"The British Guidelines on Asthma Management 1995 Review and Position Statement," Thorax, 52(Suppl 1):S1-21, 1997.

Collins et al., "The Use of Corticosteroids in the Treatment of Acute Asthma," Quarterly Journal of Medicine, New Series, XLIV:259-73, 1975.

Corren et al., "Twelve-Week, Randomized, Placebo-Controlled, Multicenter Study of the Efficacy and Tolerability of Budesonide and Formoterol in One Metered-Dose Inhaler Compared with Budesonide Alone and Formoterol Alone in Adolescents and Adults with Asthma," Clinical Therapeutics, 29(5):823-843, 2007.

Costain et al., "Guidelines for management of asthma in adults: I—chronic persistent asthma," BMJ, 301:651-653, 1990.

Devidayal et al., "Efficacy of nebulized budesonide compared to oral prednisolone in acute bronchial asthma," Acta Paediatr, 88:835-840, 1999.

Ebden et al., "Comparison of two high dose corticosteroid aerosol treatments, beclomethasone dipropionate (500 µg/day) and budesonide (1600 µg/day), for chronic asthma," Thorax, 41:869-874, 1986.

Ellul-Micallef and Johansson, "Acute Dose-Response Studies in Bronchial Asthma with a New Corticosteroid, Budesonide," Br. J. Clin. Pharmac, 15:419-422, 1983.

Ellul-Micallef et al., "Budesonide: A New Corticosteroid in Bronchial Asthma," Eur J Respir Dis., 61:167-173, 1980.

Engel et al., "Single-dose inhaled budesonide in subjects with chronic asthma," Allergy, 46:547-553, 1991.

Fanta et al., "Glucocorticoids in Acute Asthma," American Journal of Medicine, 74:845-851, 1983.

"FDA recommends easier-to-take asthma drug" Florida Today, Associate Press, Nov. 24, 1999.

"Foradil: Fast relief that lasts," Ciba-Geigy Limited, Switzerland, Medical and Pharmaceutical Information, 1993.

Hekking et al., "Efficacy and tolerability of inhaled formoterol compared with inhaled salbutamol over three months", Symposium held during the 8th congress of the European Society of Pneumology, Freiberg, Germany, Sep. 1989.

Hett et al., "Large-Scale Synthesis of Enantic- and Diasteromerically Pure (R,R)-Formoterol," Org. Process Res. Dev., 2:96-99, 1998.

Jackson et al., "Benefit-Risk Assessment of Long-Acting $\beta_2$-Agonists in Asthma," Drug Safety, 27(4):243-270, 2004.

Kesten et al., "A Three-Month Comparison of Twice Daily Inhaled Formoterol Versus Four Times Daily Inhaled Albuterol in the Management of Stable Asthma," Am Rev Respir Dis, 144:622-625, 1991.

Kumar et al., "Transient Effect of Inhaled Fluticasone on Airway Mucosal Blood Flow in Subjects with and without Asthma," Am J Respir Crit Care Med, 161:918-921, 2000.

Lampa et al., "Antitracheobronchospastic Interaction In Vitro and In Vivo between Salbutamol and Flunisolide," Drugs Exptl. Clin. Res., XI(9):653-658, 1985.

Li, "Key Points of the new asthma guidelines," The Journal of Respiratory Diseases, 18:823-838, 1997.

McDonald et al., "Evaluation of the combination inhaler of salbutamol and beclomethasone dipropionate in the management of asthma," Curr. Med. Res. Opin., 11(2), 1988.

McFadden, "Inhaled Glucocorticoids and Acute Asthma: Therapeutic Breakthrough or Nonspecific Effect?," Am J Respir Crit Care Med, 157:677-678, 1998.

Monthly Index of Medical Specialties (MIMS), Asthma, COPD, Sep. 2007.

Monthly Index of Medical Specialties (MIMS), Bronchodilators and anti-inflammatories, Dec. 1991.

Monthly Index of Medical Specialties (MIMS), Respiratory System, Dec., 1991.

Moore et al., "Long-acting Inhaled ,$\beta_2$-Agonists in Asthma Therapy," Chest, 113:1095-1108, 1998.

Nana et al., "High-Dose Inhaled Budesonide May Substitute for Oral Therapy After an Acute Asthma Attack," Journal of Asthma, 35:647-655, 1998.

National Asthma Education and Prevention Program, "Guidelines for the Diagnosis and Management of Asthma," Expert Panel Report Jul. 2, 1997 No. 97-4051.

Nyholm et al., "Therapeutic advantages of twice-daily over four-times daily inhalation budesonide in the treatment of chronic asthma," Eur J Respir Dis, 65:339-345, 1984.

The Patents Act 1953 Exhibit "CRWB1." 1998.
The Patents Act 1953 Exhibit "CRWB3." 1998.
The Patents Act 1953 Exhibit "CRWB4." 1998.
The Patents Act 1953 Exhibit "CRWB5." 1998.
The Patents Act 1953 Exhibit "CRWB6." 1998.

Poitiek et al., "Comparison of formoterol, salbutamol and salmeterol in methacholine-induced severe bronchoconstriction" $B_2$-Agonists in Methacholine-Induced Bronchoconstriction, Eur Respir J., 13:988-992, 1999.

Rabe et al., "Effect of budesonide in combination with formoterol for reliever therapy in asthma exacerbations: a randomized controlled, double-blind study," Lancet, 368:744-753, 2006.

Rabe et al., "Budesonide/Formoterol in a Single Inhaler for Maintenance and Relief in Mild-to-Moderate Asthma," Chest, 129:246-256, 2006.

Rees, "$\beta_2$ Agonists and asthma," BMJ, 302:1166-1167, 1991.

Rosenborg et al., "Relative systemic dose potency and tolerability of inhaled formoterol and salbutamol in healthy subjects and asthmatics," Eur J. Clin Pharmacol., 56:363-370, 2000.

Rodrigo et al., "Inhaled Flunisolide for Acute Severe Asthma," Am J Respir Crit Care Med, 157:698-703, 1998.

Rodrigo et al., "Acute Asthma in Adults: A Review," Chest, 125:1081-1102, 2004.

Ryrfeldt et al., "Pulmonary disposition of the potent glucocorticoid budesonide evaluated in an isolated perfused rat lung model," Biochem Pharmacol., 38:17-22, 1989.

Schuh et al., "A Comparison of Inhaled Fluticasone and Oral Prednisone for Children with Severe Acute Asthma," New England Journal of Medicine, 343:689-694, 2000.

Sears et al., "Regular inhaled beta-agonist treatment in bronchial asthma," Lancet, 336:1391-1396, 1990.

Shepherd et al., "Regular Versus Symptomatic Aerosol Bronchodilator Treatment of Asthma", Br. J. Dis. Chest, vol. 75, pp. 215-217 (1981).

Sue et al., "A Comparison of Intravenous Hydrocortilone, Methylprednisolone, and Dexamethasone in Acute Bronchial Asthma," Annals of Allergy, 56:406-409, 1986.

Sykes et al., "A study of the duration of the bronchodilator effect of 12 ug and 24 ug of inhaled formoterol and 200 ug inhaled salbutamol in asthma," Respir. Med., 84:135-138, 1990.

Tan et al., "Systemic Corticosteroid Rapidly Reverses Bronchodilator Subsensitivity induced by Formoterol in Asthmatic Patient", Am. J. Respiratory and Critical Care Medicine, 156:28-35, 1997.

Tattersfield et al. on behalf of the Facet International Study Group, "Exacerbations of Asthma," Am J Respir Crit Care Med, 160:594-599, 1999.

The Dialog Corporation, "Formoterol launched in Switzerland", Accession No: S002557609000, Oct. 31, 1990.

The Merck Manual of Diagnosis and Therapy, 16th edition, 1992, p. 653.

Trechsel, "Foradil in medical practice: 7 case studies," Ciba-Geigy Limited, Switzerland (1992).

Treschel, AM Conference Report, A new long-acting beta-stimulator, 1991.

U.S. Department of Health and Human Services, "Practical Guide for the Diagnosis and Management of Asthma," Oct. 1997 NIH Publication No. 97-4053.

Vanzieleghem et al., "A comparison of budesonide and beclomethasone dipropionate nasal aerosols in ragweed-induced rhinitis," J. Allergy Clin. Immunology, 79:887-892, 1987.

Waalkens et at, "Budesonide and terbutaline or terbutaline alone in children with mild asthma: effects on bronchial hyperresponsiveness and diurnal variation in peak flow," Thorax, 46:499-503, 1991.

Wallin et al., "Formoterol, a new long acting $beta_2$ agonist for inhalation twice daily, compared with salbutamol in the treatment of asthma," Thorax, 45:259-261, 1990.

N.C. Barnes, "Inhaled steroids in COPD", The Lancet, vol. 351, pp. 766-767 (1998).

Bourbeau et al., "Randomised controlled trial of inhaled corticosteroids in patients with chronic obstructive pulmonary disease", Thorax, vol. 53, pp. 477-482 (1998).

Corden and Rees, "The effect of oral corticosteroids on bronchodilator responses in COPD", Respiratory Medicine, vol. 92, pp. 279-282 (1998).

Paggiaro et al., "Multicentre randomised placebo-controlled trial of inhaled fluticasone propionate in patients with chronic obstructive pulmonary disease", The Lancet, vol. 351, pp. 773-780 (1998).

Watson et al., "Failure of Inhaled Corticosteroids to Modify Bronchoconstrictor or Bronchodilator Responsiveness in Middle-Aged Smokers with Mild Airflow Obstruction", CHEST, vol. 101(2), pp. 350-355 (1992).

Wempe et al., "Effects of corticosteroids on bronchodilator action in chronic obstructive lung disease", Thorax, vol. 47, pp. 616-621 (1992).

Ankerst et al., "Tolerability of a High Dose of Budesonide/Formoterol in a Single Inhaler in Patients with Asthma," manuscript (24 pages), as submitted for publication to Pulm. Pharm. Ther. with letter dated Feb. 6, 2003 to the EPO, later published as vol. 16(3), pp. 147-151 (2003).

Ankerst et al., "Tolerability of a High Dose of Budesonide/Formoterol in a Single Inhaler in Patients with Asthma," Pulm. Pharm. Ther. vol. 16(3):147-151 (2003) (abstract only).

Bjermer et al., "Long-acting (β2-agonists: how they are used in an optimal way?," Respiratory Medicine, vol. 91, pp. 587-591 (1997).

Clinical Practice Guidelines, Expert Panel Report 2, Guidelines for the Diagnosis and Management of Asthma, NIH Publication No. 97-4051, Jul. 1997.

Haughney et al., "Adjustable maintenance treatment with budesonide/formoterol combination rapidly improves and maintains quality of life in asthma patients," European Respiratory Society as Annual Congress (ERS) Stockholm, Sep. 14-18, 2002, Poster Presentation, P379, submitted to EPO with letter dated Feb. 6, 2003.

Ind et al., "Managed Adjustable closing of budesonide/formoterol combination provides equivalent asthma control to fixed dosing at a lower overall dose," European Respiratory Society Annual Congress (ERS) Stockholm, Sep. 14-18, 2002, Poster Presentation, P2450, submitted to EPO with letter dated Feb. 6, 2003.

Letter from AstraZeneca to EPO dated Feb. 6, 2003 in EP Application 99930103.9.

Lipworth, "A Single High Dose of Budesonide Rapidly Reverses Bronchoprotective Subsensitivity and β2-Adrenocepter Down-Regulation in Patients Receiving Regular Formoterol," J. Allergy Clin. Immunol., p. S152, Section 629, Jan. 1998.

Lipworth, "Airway Subsensitivity with Long-Acting β2-Agonists," Drug Safety, vol. 16(5), pp. 295-308 (1997).

Lipworth et al., "Effects of Treatment with Formoterol on Bronchoprotection against Methacholine," Amer. J. Med., vol. 104, pp. 431-438 (1998).

Löfdahl C.G. et al., "Long-acting β2-adrenoceptor agonists: a new perspective in the treatment of asthma", The European Respiratory Journal, vol. 4, pp. 218-226 (1991).

O'Byrne et al., "Additive Effects of Budesonide and Formoterol in Reducing Severe Asthma Exacerbations over 12 Months," abstract of presentation given at the Jun. 1-5, 1997, Annual Meeting of Allergology and Clinical Immunology, published as abstract 266 in Allergy 52, Supp. 37-89 (1997).

Olsson et al., "Adjustable maintenance treatment of asthma with budesonide and formoterol in a single inhaler," European Respiratory Society Annual Congress (ERS) Stockholm, Sep. 14-18, 2002, Poster Presentation, P2451, submitted to EPO with letter dated Feb. 6, 2003.

Price et al., "Budesonide/formoterol with an adjustable maintenance plan costs less and is as effective as fixed dosing," European Respiratory Society Annual Congress (ERS) Stockholm, Sep. 14-18, 2002, Poster Presentation, P2452, submitted to EPO with letter dated Feb. 6, 2003.

Rosenhall et al., "Efficacy, safety and cost of budesonide/formoterol in a single inhaler compared with budeonside plus formoterol as separate inhalers", European Respiratory Society Annual Congress (ERS) Stockholm, Sep. 14-18, 2002, Poster Presentation, P388, submitted to EPO with letter dated Feb. 6, 2003.

Scrip, The Dialog Corporation, 1562, p. 21 (Oct. 31, 1990).

Sung et al., "Randomized, Controlled Trial of Inhaled Budesonide as an Adjunct to Oral Prednisone in Acute Asthma," Academic Emergency Medicine, vol. 5(3), pp. 209-212 (1998).

Decision of the EPO Opposition Division regarding patent EP-B-1210943, dated Dec. 5, 2008.

Statement of Grounds of Opposition to patent EP1085877 by Vectura Limited, received at the EPO on Dec. 17, 2008.

Statement of Grounds of Opposition to patent EP1085877by Generics Limited, received at the EPO on Dec. 19, 2008.

Statement of Grounds of Opposition to patent EP1085877 by Norton Health Care Limited, received at the EPO on Dec. 19, 2008.

Statement of Grounds of Opposition to patent EP1085877 by Ratiopharm GmbH, received at the EPO on Dec. 17, 2008, translation attached.

What You Should Know About Symbicort Turbohaler?, AstraZeneca, May 2001, 4 pages.

U.S. Examiner Rebecca Cook, USPTO Office Action in U.S. Appl. No. 09/194,290, mailed Aug. 16, 1999 (Rescinded) (5 pages).

U.S. Examiner Rebecca Cook, USPTO Office Action in U.S. Appl. No. 09/194,290, mailed Mar. 27, 2000 (case abandoned Oct. 2, 2000) (6 pages).

U.S. Examiner Rebecca Cook, USPTO Office Action in U.S. Appl. No. 09/670,457, mailed May 10, 2001 (case abandoned Nov. 30, 2001) (6 pages).

U.S. Examiner Jennifer M. Kim, USPTO Office Action in U.S. Appl. No. 09/367,950, mailed Dec. 18, 2000 (9 pages).

Fish & Richardson P.C., Amendment in Reply to Office Action dated Dec. 18, 2001, in U.S. Appl. No. 09/367,950, filed Apr. 18, 2001 (8 pages).

U.S. Examiner Jennifer M. Kim, USPTO Final Office Action in U.S. Serial No. 09/367,950, mailed May 21, 2001 (8 pages).

Fish & Richardson P.C., Response to Final Office Action dated May 21, 2001, in U.S. Appl. No. 09/367,950, filed Aug. 21, 2001 (4 pages).

U.S. Examiner Jennifer M. Kim, USPTO Office Action in U.S. Appl. No. 09/367,950, mailed Sep. 25, 2001 (8 pages).

Fish & Richardson P.C., Response to Office Action dated May 21, 2001, in U.S. Appl. No. 09/367,950, filed Dec. 26, 2001 (3 pages).

U.S. Examiner Jennifer M. Kim, USPTO Final Office Action in U.S. Appl. No. 09/367,950, mailed Apr. 15, 2002 (6 pages).

U.S. Examiner Jennifer M. Kim, in U.S. Appl. No. 09/369,950, Interview Summary dated Sep. 17, 2002 (1 page).

Fish & Richardson P.C., Notice of Appeal in U.S. Appl. No. 09/367,950, filed Oct. 9, 2002 (1 page).

Fish & Richardson P.C., Request for Continued Examination and Amendment in Reply in U.S. Appl. No. 09/367,950, filed Dec. 10, 2002 (55 pages).

U.S. Examiner Jennifer M. Kim, USPTO Office Action in U.S. Appl. No. 09/367,950, mailed Mar. 21, 2003 (9 pages).

Fish & Richardson P.C., Response to Office Action dated Mar. 21, 2003, in U.S. Appl. No. 09/367,950, filed Jun. 19, 2003 (9 pages).

Fish & Richardson P.C., Supplemental Amendment filed Jul. 3, 2003, in U.S. Appl. No. 09/367,950 (8 pages).

U.S. Examiner Jennifer M. Kim, Notice of Allowance mailed Jul. 9, 2003, in U.S. Appl. No. 09/367,950 (9 pages).

U.S. Examiner Jennifer M. Kim, USPTO Office Action in U.S. Appl. No. 09/367,950, mailed May 4, 2004 (12 pages).
Fish & Richardson P.C., Reply to Office Action dated May 4, 2004, in U.S. Appl. No. 09/367,950 filed Nov. 1, 2004 (6 pages).
U.S. Examiner Jennifer M. Kim, USPTO Office Action in U.S. Appl. No. 09/367,950, mailed Mar. 30, 2005 (14 pages).
Fish & Richardson P.C., Amendment in Reply to Office Action dated Mar. 30, 2005, in U.S. Appl. No. 09/367,950, filed Jun. 29, 2005 (17 pages).
U.S. Examiner Jennifer M. Kim, USPTO Office Action in U.S. Serial No. 09/367,950, mailed Sep. 21, 2005 (15 pages).
Fish & Richardson P.C., Amendment in Reply to Office Action dated Sep. 21, 2005, in U.S. Serial No. 09/367,950, filed Nov. 15, 2005 (12 pages).
U.S. Examiner Jennifer M. Kim, Advisory Action in U.S. Appl. No. 09/367,950, mailed Dec. 14, 2005 (3 pages).
Fish & Richardson P.C., Brief on Appeal filed Mar. 3, 2006, in U.S. Appl. No. 09/367,950, filed Mar. 3, 2006 (61 pages).
Examiner's Answer in U.S. Appl. No. 09/367,950, mailed Jun. 16, 2006 (15 pages).
Fish & Richardson P.C., Reply Brief on Appeal filed Aug. 14, 2006, in U.S. Appl. No. 09/367,950 (15 pages).
Communication regarding Appeal Brief in U.S. Appl. No. 09/367,950, mailed Sep. 12, 2006 (2 pages).
Notice of Non-Compliant Appeal Brief in U.S. Appl. No. 09/367,950, mailed Oct. 30, 2006 (4 pages).
Fish & Richardson P.C., Amendment in Reply to Non-Compliant Appeal Brief dated Oct. 30, 2006, in U.S. Appl. No. 09/367,950 filed Nov. 28, 2006 (8 pages).
Office Communication dated Jan. 24, 2007, in U.S. Appl. No. 09/367,950 (2 pages).
Board of Appeals and Interferences, Order remanding to the Examiner, in U.S. Appl. No. 09/367,950, dated Aug. 28, 2007 (11 pages).
Interview Summary mailed Oct. 22, 2007, in U.S. Appl. No. 09/367,950 (4 pages).
Fish & Richardson P.C., Interview Summary Following Board Decision of Aug. 28, 2007, dated Nov. 9, 2007 and re-filed Nov. 21, 2007 in U.S. Appl. No. 09/367,950 (13 pages).
Office Action in U.S. Appl. No. 09/367,950, mailed Dec. 4, 2007 (16 pages).
Fish & Richardson P.C., Amendment in Reply to Office Action dated Dec. 4, 2007, in U.S. Appl. No. 09/367,950 filed Jun. 3, 2008 (37 pages).
Final Office Action in U.S. Appl. No. 09/367,950, mailed Oct. 6, 2008 (21 pages).
Fish & Richardson P.C., Amendment in Reply to Final Office Action dated Oct. 6, 2008, in U.S. Appl. No. 09/367,950 filed Apr. 3, 2009 (20 pages).
Office Action in U.S. Appl. No. 10/665,240, mailed Jan. 30, 2007 (18 pages).
Fish & Richardson P.C., Amendment in Reply to Final Office Action dated Jan. 30, 2007, in U.S. Appl. No. 10/665,240, filed Jul. 27, 2007 (30 pages).
Final Office Action in U.S. Appl. No. 10/665,240, mailed Oct. 18, 2007 (25 pages).
Fish & Richardson P.C., Amendment in Reply to Final Office Action dated Oct. 18, 2007 in U.S. Appl. No. 10/665,240, filed Apr. 17, 2008 (14 pages).
Advisory Action Before the Filing of an Appeal Brief in U.S. Appl. No. 10/665,240, dated May 5, 2008 (5 pages).
Final Office Action in U.S. Appl. No. 10/665,240, mailed Sep. 19, 2008 (16 pages).
Fish & Richardson P.C., Amendment in Reply to Final Office Action dated Sep. 19, 2008, in U.S. Appl. No. 10/665,240, filed Mar. 18, 2009 (21 pages).
Final Office Action in U.S. Appl. No. 10/665,240, mailed June 12, 2009 (25 pages).
Office Action from U.S. Appl. No. 09/367,950, mailed June 25, 2009 (21 pages).
D.C. Flenley, "Today's Treatment of Airway Obstruction . . . and Tomorrow's?", Respiration, pp. 4-9 (1989).
Rabe et al., "The challenge of long-acting β-adrenoceptor agonists", Respiratory Medicine, vol. 85, pp. 5-9 (1991).

Notice of Opposition, filed by Ranbaxy Laboratories Limited, opposing the grant of Patent Application No. 190791 by Intellectual Property India (India Patent Office), dated Jun. 1, 2006 (21 pages).
Reply statement before the Opposition Board, Patent Office, Delhi; submitted on behalf of AstraZeneca, dated Jul. 27, 2006 (6 pages).
Affidavit of Jan William Trofast, before the Opposition Board, Patent Office, Delhi; submitted on behalf of AstraZeneca, dated Sep. 13, 2006 (7 pages).
Opponent Response in Opposition to Patent No. 19071, submitted by Lakshmi Kumaran & Sridharan, dated Nov. 3, 2006 (6 pages).
Response to EPO Office Action in opposition against EP 108577, sent by AstraZeneca, dated Oct. 5, 2009 (17 pages).
Rabe et al., "Effect of budesonide in combination with formoterol for reliever therapy in asthma exacerbations: a randomized controlled, double-blind study," The Lancet, vol. 368, pp. 744-753 (2006) and slides based on Rabe et al.
Product insert for Advair Diskus®, Patient's Instructions for Use (3 pages).
Product insert for Symbicort® Turbuhaler® (2 pages).
Product insert for Pulmicort Turbuhaler® (4 pages).
Barnes, "A Single Inhaler for Asthma?," American Journal of Respiratory and Critical Care Medicine, vol. 171, pp. 95-96 (2005).
O'Bryne et al., "Budesonide/Formoterol Combination Therapy as Both Maintenance and Reliever Medication in Asthma," American Journal of Respiratory and Critical Care Medicine, vol. 171, pp. 129-136 (2005).
Chapter 2, Six-Part Asthma Management Program (International Consensus Report on Diagnosis and Management of Asthma), Allergy, vol. 47, suppl. 13, pp. 6-49 (1992).
Health Facts for You, Asthma Rescue Medicine, University of Wisconsin, Mar. 31, 2008 (2 pages).
Anthony D. D'Urzo, "Inhaled Glucocorticosteroid and Long-Acting $\beta_2$ Adrenoceptor Agonist Single-Inhaler Combination for Both Maintenance and Rescue Therapy", Treat. Respir. Med., vol. 5(6), pp. 385-391 (2006).
Kuna et al., "Effect of budesonide/formoterol maintenance and reliever therapy on asthma exacerbations", International Journal of Clinical Practice, vol. 61(5), pp. 725-736 (2007), and slides based on Kuna.
Tierney, et al., Disorders of the Airways, Current Medical Diagnosis and Treatment, Chapter 9, pp. 241-255, (1997).
Renkema et al., "Effects of Long-term Treatment With Corticosteroids in COPD," Chest, vol. 109, pp. 1156-1162 (1996).
Cochrane et al., "Bronchial asthma and the role of $\beta_2$-agonists", Respiratory Medicine, vol. 91(5), pp. 275-279 (1997).
Wilcke et al., "The effect of inhaled glucocorticosteroids in emphysema due to $\alpha_1$-antitrypsin deficiency", Respiratory Medicine, vol. 91, pp. 275-279 (1997).
Smeenk et al., Opportunistische longinfecties bij patiënten met chronishe obstructieve longziekte; een bijwerking van inhalatiecorticosteroïden?, English translation included, dated Mar. 11, 2003.
Wyser et al., Neu Aspekte in der Behandlung des Asthma bronchiale and chronisch obstruktiver Lungenkrankheiten, Schweiz-Med Wochenschr, vol. 127, pp. 885-890 (1997), English Summary included.
"Ventide Inhaler," ABPI Data Sheet Compendium, 1990-91 (3 pages).
Barnes, "A New Approach to the Treatment of Asthma," Drug Therapy, vol. 321(22), pp. 1517-1527 (2002).
"Foradil: Fast relief that lasts," Ciba-Geigy Limited, Switzerland, Medical and Pharmaceutical Information, Update 1994 (51 pages).
English Translation of Opposition filed against Chilean Patent Application No. 2744-2001 (3 pages).
Response to an Opposition in Chilean Application No. 2744/2001, dated Aug. 6, 2006, English Translation included (6 pages).
Request for Revocation of the Corresponding Patent in Turkey (TR 2000 00726), dated Jun. 6, 2009 (15 pages).
Fish & Richardson P.C., Reply to Office Action in U.S. Appl. No. 10/665,240, filed Dec. 11, 2009 (12 pages).
Fish & Richardson P.C., Reply to Office Action in U.S. Appl. No. 09/367,950, filed Dec. 21, 2009 (14 pages).

EPO Office Action from EP Serial No. 03 002 381.6-2123, dated Jun. 7, 2010 (5 pages).
Fish & Richardson P.C., Response to Final Office Action, in U.S. Appl. No. 09/367,950, filed Jun. 16, 2010 (22 pages).
Final Office Action in U.S. Appl. No. 10/665,240, mailed Aug. 20, 2010 (26 pages).
Final Office Action in U.S. Appl. No. 09/367,950, mailed Mar. 17, 2010 (19 pages).
Fish & Richardson Response to Office Action in U.S. Appl. No. 10/665,240, mailed Mar. 4, 2010, filed Jun. 3, 2010 (24 pages).
Barnes, "Chronic Obstructive Pulmonary Disease," Medical Progress, vol. 343(4), pp. 269-280 (2000).
Bateman et al, "Overall asthma control: The relationship between current control and future risk," J. Allergy Clin. Immunol., vol. 125(3), pp. 600-608e6 (2010).
Bousquet et al., "Budesonide/formoterol for maintenance and relief in uncontrolled asthma vs. high-dose salmeterol/fluticasone," Respiratory Medicine, vol. 101, pp. 2437-2446 (2007).
BTS Guidelines for the Management of Chronic Obstructive Pulmonary Disease, Thorax, vol. 52(a), pp. S1-S28 (1997).
Calverley et al., "Preventing mortality in Copd: The value of inhaled budesonide added to bronchodilators." Presentation at COPD5, Birmingham, UK, 28 Jun. 2006, Abstract 35.
Cates et al. "Combination formoterol and budesonide as maintenance and reliever therapy versus inhaled steroid maintenance for chronic asthma in adults and children (Review)," Published by Wiley and Sons, Ltd., 64 pp. (2010).
Chapman, "SMART isn't," J. Allergy Clin. Immunol., vol. 125, pp. 609-610 (2010).
Dalby et al., "The bioavailability and airway clearance of the steroid component of budesonide/formoterol and salmeterol/fluticasone after inhaled administration in patients with COPD and healthy subjects: a randomized controlled trial," Respiratory Research, vol. 10(104), pp. 1-11 (2009).
Definitions, Epidemiology, Pathophysiology, Diagnosis, and Staging, American Journal of Respiratory and Critical Care Medicine, vol. 152, pp. S78-S121 (1995).
D'Urzo, "Inhaled Glucocorticosteroid and Long-Acting β2-Adrenoceptor Agonist Single-Inhaler Combination for Both Maintenance and Rescue Therapy," Treat Respir Med 5:385-391 (2006).
Edwards et al., "Budesonide/formoterol for maintenance and reliever therapy of asthma: a meta analysis of randomised controlled trials," The International Journal of Clinical Practice, vol. 64(5), pp. 619-627 (2010).
Jones et al., "St George's respiratory questionnaire (SGRQ) scores may help identify COPD patients at increased risk of death over 1 year." Presentation at COPD5, Birmingham, UK, Jun. 28, 2006, Abstract 34.
Kuna et al., "Effect of budesonide/formoterol maintenance and reliever therapy on asthma exacerbations," Int. J. Clin. Pract., vol. 61(5), pp. 725-736 (2007).

Martin and Kraft, ed., *Combination Therapy for Asthma and Chronic Obstructive Pulmonary Disease*, Marcel Dekker, Inc., 2000, pp. 274-293.
Partridge et al., "Effect on lung function and morning activities of budesonide/formoterol versus salmeterol/fluticasone in patients with COPD," Therapeutic Advances in Respiratory Disease, vol. 3(4), pp. 147-157 (2009).
Pavord et al., "Airway inflammation in patients with asthma with high-fixed or low-fixed plus as-needed budesonide/formoterol," J. Allergy Clin. Immunol., vol. 123(5), pp. 1083-1089.e7 (2009).
Product Information for "Foradil Dosis-aerosol," Netherlands authorization date Mar. 4, 1992, Medicines Data Bank (downloaded from the Internet on Jan. 28, 2005), followed by a nine-page printout from the register of the Medicines Evaluation Board of the Netherlands regarding formoterol fumerate dihydrate, dated Jul. 15, 2003, pp. 1-9.
Rabe et al., "Effect of budesonide in combination with formoterol for reliever therapy in asthma exacerbations: a randomised controlled, double-blind study," The Lancet, vol. 368, pp. 744-753 (2006).
Rennard et al., "Efficacy and Tolerability of Budesonide/Formoterol in One Hydrofluoroalkane Pressurized Metered-Dose Inhaler in Patients with Chronic Obstructive Pulmonary Disease," Drugs, vol. 69(5), pp. 549-565 (2009).
Scicchitano et al., "Efficacy and safety of budesonide/formoterol single inhaler therapy versus a higher dose of budesonide in moderate to severe asthma," Current Medical Research and Opinion, vol. 20(9), pp. 1403-1418 (2004).
Siafakas et al., "Optimal assessment and management of chronic obstructive pulmonary disease (COPD)," European Respiratory Journal, vol. 8, pp. 1398-1420 (1995).
Tashkin et al., "Efficacy and Safety of Budesonide and Formoterol in One Pressurized Metered-Dose Inhaler in Patients with Moderate to Very Severe Chronic Obstructive Pulmonary Disease," Drugs, vol. 68(14); pp. 1975-2000 (2008).
Taylor, et al., "A new perspective on concepts of asthma severity and control," Eur. Respir. J. vol. 32, pp. 545-554 (2008).
Urbano, "Review of the Naepp 2007 Expert Panel Report (EPR-3) on Asthma Diagnosis and Treatment Guidelines," Journal of Managed Care Pharmacy, vol. 14(1), pp. 41-49 (2008).
Wasserman, "What Is a Rescue Medicine and When Is It Used to Treat Asthma?," ABC News, 2 pages (2008).
Venner Shipley LLP, Letter to the European Patent Office regarding opposition to EP Patent No. 1085877, filed by Generics (UK) Limited (Apr. 20, 2010).
Welte et al., "Efficacy and Tolerability of Budesonide/Formoterol Added to Tiotropium in Patients with Chronic Obstructive Pulmonary Disease," Am. J. Respir. Crit. Care Med., vol. 180, pp. 741-750 (2009).
D.C. Flenley, "Today's Treatment of Airway Obstruction . . . And Tomorrow's?", Respiration, pp. 4-9 (1989).
Rabe et al., "The challenge of long-acting β-adrenoceptor agonists", Respiratory Medicine, vol. 85, pp. 5-9 (1991).
Office Action in U.S. Appl. No. 10/665,240, mailed Mar. 4, 2010 (27 pages).

* cited by examiner

USE FOR BUDESONIDE AND FORMOTEROL

This application is a continuation of U.S. Ser. No. 09/670,457, filed Sep. 26, 2000 (now abandoned), which is a continuation of U.S. Ser. No. 09/194,290, filed Nov. 23, 1998 (now abandoned), which is the National Stage application of International Application No. PCT/SE98/01599, filed Sep. 9, 1998, which claims the benefit of Swedish Patent Application No. 9703407-8, filed Sep. 19, 1997. The contents of these applications are incorporated herein by reference in their entirety.

FIELD OF THE INVENTION

The invention provides the use of formoterol and budesonide in the treatment of chronic obstructive pulmonary disease (COPD).

BACKGROUND OF THE INVENTION

Chronic obstructive pulmonary disease (COPD) is a term which refers to a large group of lung diseases which can interfere with normal breathing. It is estimated that 11% of the U.S. population has COPD and the incidence is increasing. The two most important conditions covered by COPD are chronic bronchitis and emphysema.

Chronic bronchitis is a long-standing inflammation of the bronchi which causes increased production of mucous and other changes. The patients' symptoms are cough and expectoration of sputum. Chronic bronchitis can lead to more frequent and severe respiratory infections, narrowing and plugging of the bronchi, difficult breathing and disability.

Emphysema is a chronic lung disease which affects the alveoli and/or the ends of the smallest bronchi. The lung loses its elasticity and therefore these areas of the lungs become enlarged. These enlarged areas trap stale air and do not effectively exchange it with fresh air. This results in difficult breathing and may result in insufficient oxygen being delivered to the blood. The predominant symptom in patients with emphysema is shortness of breath.

At present moderate to severe COPD is treated with a variety of monotherapies including inhaled or orally administered bronchodilators, inhaled anti-cholinergic agents and orally administered steroids, especially corticosteroids. The problem with these treatments is that none of them is especially effective. For example, many patients with COPD have a reversible component. Accordingly a new treatment is required for decreasing the intensity of exacerbations, thereby improving the lung function of patients suffering from COPD.

DESCRIPTION OF THE INVENTION

It has surprisingly been found that the combination of formoterol and budesonide is effective in treating COPD.

The combination of budesonide and formoterol reduces the number of exacerbations of COPD compared to the monotherapies using budesonide or formoterol, thereby improving the lung function of the patients. Thus, the combination of budesonide and forrmoterol will give greater compliance, greater efficacy, less exacerbations and/or better sleep.

The present invention also gives an increased compliance and efficacy and thereby quality of life.

According to the invention there is provided the use of a composition comprising, in admixture or separately:

(a) a first active ingredient which is formoterol, a pharmaceutically acceptable salt or solvate thereof, or a solvate of such a salt;
(b) a second active ingredient which is budesonide; and
a molar ratio of the first active ingredient to the second active ingredient of from 1:2500 to 12:1, in the manufacture of a medicament for use in the treatment of chronic obstructive pulmonary disease.

The composition used in the invention optionally additionally comprises one or more pharmaceutically acceptable additives, diluents and/or carriers. The composition is preferably in the form of a dry powder, wherein the particles of the pharmaceutically active ingredients preferably have a mass median diameter of less than 10 μm.

The invention also includes the use of a kit containing:
(i) a vessel containing the first active ingredient;
(ii) a vessel containing the second active ingredient;
(iii) a molar ratio of the first active ingredient to the second active ingredient of from 1:2500 to 12:1; and
(iv) instructions for the simultaneous, sequential or separate administration of the active ingredients to a patient in need thereof;

in the manufacture of a medicament for use in the treatment of chronic obstructive pulmonary disease.

A patient suffering from COPD can be treated by administering via inhalation a composition as defined above. Alternatively such a patient can be treated by administering via inhalation, simultaneously, sequentially or separately, (i) a dose of the first active ingredient; and (ii) a dose of the second active ingredient. The molar ratio of the first active ingredient to the second active ingredient is from 1:2500 to 12. The doses can be provided to the patient for inhalation in dry powder form.

The invention further provides the use of budesonide and of formoterol in the manufacture of a composition or a kit, as used in the invention, for use in the treatment of chronic obstructive pulmonary disease.

The first and second active ingredients of the kit used in the invention can be administered simultaneously, sequentially or separately to COPD. By sequential is meant that the first and second active ingredients are administered one after the other. They still have the desired effect if they are administered separately but less than about 12 hours apart, preferably less than about 2 hours apart, more preferably less than about 30 minutes apart, and most preferably one immediately after the other.

The molar ratio of the first active ingredient to the second active ingredient is suitably from 1:555 to 2:1 and preferably from 1:150 to 1:1. The molar ratio of the first active ingredient to the second active ingredient is more preferably from 1:133 to 1:6. The molar ratio of the first active ingredient to the second active ingredient can also be 1:70 to 1:4.

Preferably the amount of the first active ingredient used is preferably from 2 to 120 nmol (more preferably from 7 to 70 nmol). The amount of the second active ingredient used is preferably from 0.1 to 5 μmol (preferably 0.15 to 4 μmol) or from 45 to 2200 μg, more preferably from 65 to 1700 μg.

Throughout the specification, the amount of the first and second active ingredient used relate to unit doses unless explicitly defined differently.

Suitable physiologically acceptable salts of formoterol include acid addition salts derived from inorganic and organic acids, for example the chloride, bromide, sulphate. phosphate, maleate, fumarate, tartrate, citrate, benzoate, 4-methoxybenzoate, 2- or 4-hydroxybenzoate, 4-chlorobenzoate, p-toluenesulphonate, methanesulphonate, ascorbate, acetate, succinate, lactate, glutarate, gluconate, tricarballylate, hydroxynaphthalene-carboxylate or oleate salts or solvates thereof. The first active ingredient is preferably formoterol fumarate, especially the dihydrate thereof.

When the first active ingredient is formoterol fumarate dihydrate, the amount of the first active ingredient used is suitably from 1 to 50 µg, more suitably from 3 to 30 µg.

Preferably the composition or kit used in the invention comprises unit doses of 6 µg of formoterol fumarate dihydrate and 100 µg of budesonide, or 4.5 µg of formoterol fumarate dihydrate and 80 µg of budesonide, either of which is administered up to four times a day. Alternatively the composition or kit of the invention comprises unit doses of 12 µg of formoterol fumarate dihydrate and 200 µg of budesonide, or 9 µg of formoterol fumarate dihydrate and 160 µg of budesonide, either of which is administered once or twice a day.

More preferably the composition or kit used in the invention comprises unit doses of 6 µg of formoterol fumarate dihydrate and 200 µg of budesonide, or 4.5 µg of formoterol fumarate dihydrate and 160 µg of budesonide, either of which is administered up to four times a day. Alternatively the composition or kit of the invention comprises unit doses of 12 µg of formoterol fumarate dihydrate and 400 µg of budesonide, or 9 µg of formoterol fumarate dihydrate and 320 µg of budesonide, either of which is administered once or twice a day.

Most preferably the composition or kit used in the invention comprises unit doses of 6 µg of formoterol fumarate dihydrate and 400 µg of budesonide, or 4.5 µg of formoterol fumarate dihydrate and 320 µg of budesonide, either of which is administered up to four times a day.

Preferably the active ingredient(s) are used in admixture with one or more pharmaceutically acceptable additives, diluents or carriers, preferably in an amount of from 50 µg to 25 mg per dose. more preferably in an amount of from 50 µg to 10 mg, most preferably in an amount of from 100 to 2000 µg per unit dose. Examples of suitable diluents or carriers include lactose, dextran, mannitol or glucose. Preferably lactose is used, especially as the monohydrate.

One or more of the ingredients is preferably in the form of a dry powder, more preferably a finely divided powder, e.g. micronised dry powder, most preferably an agglomerated micronised dry powder. As an alternative to agglomeration, the finely divided active ingredients may be in the form of an ordered mixture with the pharmaceutically acceptable additive, diluent or carrier. An ordered mixture comprises fine particles of an active ingredient in association with coarse particles or a mixture of coarse and finely divided particles of the pharmaceutically acceptable additive, diluent or carrier. The ingredients used in the invention can be obtained in these preferred forms using methods known to those of skill in the art. The particle size of the active ingredients is preferably less than 10 µm.

Administration may be by inhalation orally or intranasally. The active ingredients are preferably adapted to be administered, either together or individually, from dry powder inhaler(s) (DPIs), especially Turbuhaler® (Astra AB), pressurised metered dose inhaler(s) (pMDIs), or nebuliser(s).

When the active ingredients are adapted to be administered, either together or individually, from pressurised inhaler(s), they are preferably in finely divided, and more preferably in micronised form. They may be dissolved or, preferably, suspended in a liquid propellant mixture. The propellants which can be used include chlorofluorocarbons, hydrocarbons or hydrofluoroalkanes. Especially preferred propellants are P134a (tetrafluoroethane) and P227 (heptafluoropropane) each of which may be used alone or in combination. They are optionally used in combination with one or more other propellants and/or one or more surfactants and/or one or more other excipients, for example ethanol, a lubricant, an antioxidant and/or a stabilising agent.

When the active ingredients are adapted to be administered, either together or individually, via nebuliser(s) they may be in the form of a nebulised aqueous suspension or solution, with or without a suitable pH or tonicity adjustment, either as a unit dose or multidose device.

The composition or kit used in the invention may optionally be administered as divided doses from 1 to 4, and preferably once or twice a day.

The invention is illustrated by the following Examples which are not intended to limit the scope of the application. In the Examples micronisation is carried out in a conventional manner such that the particle size range for each component is suitable for administration by inhalation. Turbuhaler® is a trademark of Astra AB.

EXAMPLE 1

6 Parts by weight of formoterol fumarate dihydrate was mixed with 794 parts. by weight of lactose monohydrate. The blend was micronised using a high pressure air jet mill and then conditioned using the process of EP-A-717 616. 200 Parts by weight of micronised budesonide was added to the conditioned product by mixing and homogenising with a low pressure jet mill. The mixture was then spheronised using the process of EP-A-721 331 and filled into the storage compartment of a Turbuhaler® dry powder inhaler.

EXAMPLE 2

4.5 Parts by weight of formoterol fumarate dihydrate was mixed with 835 parts by weight of lactose monohydrate. The blend was micronised using a high pressure air jet mill and then conditioned using the process of EP-A-717 616. 160 Parts by weight of micronised budesonide was added to the conditioned product by mixing and homogenising with a low pressure jet mill. The mixture was then spheronised using the process of EP-A-721 331 and filled into the storage compartment of a Turbuhaler® dry powder inhaler.

EXAMPLE 3

12 Parts by weight of formoterol fumarate dihydrate was mixed with 588 parts by weight of lactose monohydrate. The blend was micronised using a high pressure air jet mill and then conditioned using the process of EP-A-717 616. 400 Parts by weight of micronised budesonide was added to the conditioned product by mixing and homogenising with a low pressure jet mill. The mixture was then spheronised using the process of EP-A-721 331 and filled into the storage compartment of a Turbuhaler® dry powder inhaler.

EXAMPLE 4

6 Parts by weight of formoterol fumarate dihydrate was mixed with 894 parts by weight of lactose monohydrate. The blend was micronised using a high pressure air jet mill and then conditioned using the process of EP-A-717 616. 100 Parts by weight of micronised budesonide was added to the conditioned product by mixing and homogenising with a low pressure jet mill. The mixture was then spheronised using the process of EP-A-721 331 and filled into the storage compartment of a Turbuhaler® dry powder inhaler.

EXAMPLE 5

4.5 Parts by weight of formoterol fumarate dihydrate was mixed with 915 parts by weight of lactose monohydrate. The blend was micronised using a high pressure air jet mill and then conditioned using the process of EP-A-717 616. 80 Parts by weight of micronised budesonide was added to the conditioned product by mixing and homogenising with a low pressure jet mill. The mixture was then spheronised using the proces EP-A-721 331 and filled into the storage compartment of a Turbuhaler® dry powder inhaler.

EXAMPLE 6

12 Parts by weight of formoterol fumarate dihydrate was mixed with 788 parts by weight of lactose monohydrate. The blend was micronised using a high pressure air jet mill and then conditioned using the process of EP-A-717 616. 200 Parts by weight of micronised budesonide was added to the conditioned product by mixing and homogenising with a low pressure jet mill. The mixture was then spheronised using the process of EP-A-721 331 and filled into the storage compartment of a Turbuhaler® dry powder inhaler.

EXAMPLE 7

6 Parts by weight of formoterol fumarate dihydrate was mixed with 994 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

200 Parts by weight of micronised budesonide was mixed with 800 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE 8

4.5 Parts by weight of formoterol fumarate dihydrate was mixed with 995 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

160 Parts by weight of micronised budesonide was mixed with 840 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE 9

12 Parts by weight of formoterol fumarate dihydrate was mixed with 988 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

400 Parts by weight of micronised budesonide was mixed with 600 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE 10

6 Parts by weight of formoterol fumarate dihydrate was mixed with 994 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

100 Parts by weight of micronised budesonide was mixed with 900 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE 11

4.5 Parts by weight of formoterol fumarate dihydrate was mixed with 995 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

80 Parts by weight of micronised budesonide was mixed with 920 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE 12

12 Parts by weight of formoterol fumarate dihydrate was mixed with 988 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

200 Parts by weight of micronised budesonide was mixed with 800 parts by weight of lactose monohydrate. The blend was micronised using a high pressure air jet mill and then conditioned using the process of EP-A-717 616. The mixture was then spheronised using the process of EP-A-721 331 and filled into the storage compartment of a Turbuhaler® dry powder inhaler.

EXAMPLE A

Patients suffering from COPD are first put through a run-in period of 2 weeks and are then split into 4 groups of approximately equal numbers. Each group is then given either budesonide/formoterol, budesonide alone, formoterol alone or placebo for a period of 12 months.

The following parameters for each patient are monitored throughout: mild and severe exacerbations, $FEV_1$ (forced expiratory volume in one second), vital capacity (VC), peak expiratory flow (PEF), symptom scores and Quality of Life. Of these, mild and severe exacerbations are considered to be primary efficacy variables, whereas the remaining parameters are considered to be secondary efficacy variables.

The invention claimed is:

1. A method for reducing the frequency and/or intensity of chronic obstructive pulmonary disease (COPD) exacerbations experienced by a patient suffering from COPD, which method comprises administering to the patient via inhalation (i) a first active ingredient which is formoterol, a pharmaceutically acceptable salt or solvate thereof, or a solvate of such a salt; and (ii) a second active ingredient which is budesonide, wherein the method is effective to reduce the frequency and/or intensity of exacerbations in the patient, the first and second active ingredients are administered simultaneously, and the molar ratio of (a) formoterol in the first active ingredient to (b) the second active ingredient is from 1:555 to 2:1.

2. A method according to claim 1, wherein the first and/or second active ingredient is used in admixture with one or more pharmaceutically acceptable additives, diluents and/or carriers.

3. A method according to claim 1, wherein the first active ingredient is formoterol fumarate dihydrate.

4. A method according to claim 1, wherein the molar ratio is from 1:133 to 1:6.

5. A method according to claim 4 wherein the molar ratio is from 1:70 to 1:4.

6. A method according to claim 1, wherein the first and second active ingredients are provided in powder form.

7. A method according to claim 6 wherein the first and second active ingredients are formulated as powder particles having a mass median diameter of less than 10 μm.

8. A method according to claim 1 wherein the first and second active ingredients are provided in the form of an admixture.

9. A method according to claim 1 wherein the first active ingredient is administered to the patient in one or more unit doses per day, the amount of formoterol delivered to the patient by each unit dose of the first active ingredient being from about 2 to 120 nmol.

10. A method according to claim 9 wherein the amount of formoterol delivered to the patient by each unit dose of the first active ingredient is from about 7 to 70 nmol.

11. A method according to claim 1 wherein the second active ingredient is administered to the patient in one or more unit doses per day, the amount of budesonide delivered to the patient by each unit dose being from about 0.1 to 5 μmol.

12. A method according to claim 11 wherein the amount of budesonide delivered to the patient by each unit dose is from about 0.15 to 4 μmol.

13. A method according to claim 3 wherein the formoterol fumarate dihydrate is administered to the patient in one or more unit doses per day, the amount of formoterol fumarate dihydrate delivered to the patient by each unit dose being from about 1 to 50 μg.

14. The method of claim 1, further comprising monitoring the number of exacerbations experienced by the patient over a period of 12 months of treatment.

15. The method of claim 1, wherein the first active ingredient is administered in the form of one or more unit doses of formoterol fumarate dihydrate, each unit dose delivering 4.5 μg of formoterol fumarate dihydrate to the patient; and the second active ingredient is administered in the form of one or more unit doses of budesonide, each unit dose of budesonide delivering 160 μg of budesonide to the patient.

16. The method of claim 15, wherein the unit doses of both the formoterol fumarate dihydrate and the budesonide are administered one to four times per day.

17. The method of claim 1, wherein the first and second active ingredients are administered together from a pressurized metered dose inhaler (pMDI).

18. The method of claim 1, wherein at least one of the first and second active ingredients is formulated in a propellant comprising one or both of P227 (heptafluoropropane) and P134(a) (tetrafluoroethane).

19. The method of claim 3, wherein the first and second active ingredients are provided in admixture.

20. The method of claim 19, wherein the first and second active ingredients are in powder form.

21. The method of claim 20, wherein the first and second active ingredients are administered in admixture in the form of unit doses, each unit dose delivering to the patient 4.5 μg formoterol fumarate dihydrate and 160 μg budesonide.

22. The method of claim 21, wherein the patient is administered one to four of the unit doses per day.

23. The method of claim 20, wherein the first and second active ingredients are administered in admixture in the form of unit doses, each unit dose delivering to the patient 9 μg formoterol fumarate dihydrate and 320 μg budesonide.

24. The method of claim 23, wherein the patient is administered one or two of the unit doses per day.

25. The method of claim 1, wherein the first active ingredient is in the form of one or more unit doses of formoterol fumarate dihydrate, each unit dose delivering 4.5 μg of formoterol fumarate dihydrate to the patient; and the second active ingredient, which may be separate from or in admixture with the first active ingredient, is administered in the form of one or more unit doses of budesonide, each unit dose of budesonide delivering 80 μg of budesonide to the patient.

26. The method of claim 25, wherein the unit doses of both the first active ingredient and the second active ingredient are administered one to four times per day.

27. The method of claim 1, wherein the first active ingredient is administered in the form of one or more unit doses of formoterol fumarate dihydrate, each unit dose delivering 9 μg of formoterol fumarate dihydrate to the patient; and the second active ingredient, which may be separate from or in admixture with the first active ingredient, is administered in the form of one or more unit doses of budesonide, each unit dose of budesonide delivering 160 μg of budesonide to the patient.

28. The method of claim 27, wherein the unit doses of both the first active ingredient and the second active ingredient are administered once or twice per day.

29. A method for the treatment of a patient suffering from COPD, which method comprises administering to the patient via inhalation (i) a daily dose of a first active ingredient that is formoterol, a pharmaceutically acceptable salt or solvate thereof, or a solvate of such a salt, the daily dose of the first active ingredient delivering 2 to 120 nmol of formoterol to the patient; and (ii) a daily dose of a second active ingredient that is budesonide, the daily dose of the second active ingredient delivering 45 to 2200 μg of budesonide to the patient, wherein the first active ingredient, which may be separate from or in admixture with the second active ingredient, is administered simultaneously with the second active ingredient, and wherein the daily dose of each active ingredient is administered in one to four divided doses per day.

30. The method of claim 29, wherein each daily dose of the first active ingredient is administered as one or more unit doses of formoterol fumarate dihydrate, each unit dose delivering 9 μg of formoterol fumarate dihydrate to the patient; and each daily dose of the second active ingredient, which may be separate from or in admixture with the first active ingredient, is administered as one or more unit doses of budesonide, each unit dose of budesonide delivering 320 µg of budesonide to the patient.

31. The method of claim 30, wherein the unit doses of both the formoterol fumarate dihydrate and the budesonide are administered once or twice per day.

32. The method of claim 29, wherein each daily dose of the first active ingredient is administered as one or more unit doses of formoterol fumarate dihydrate, each unit dose delivering 4.5 µg formoterol fumarate dihydrate to the patient; and each daily dose of the second active ingredient, which may be separate from or in admixture with the first active ingredient, is administered as one or more unit doses of budesonide, each unit dose delivering 80 µg of budesonide to the patient.

33. The method of claim 29, wherein each daily dose of the first active ingredient is administered as one or more unit doses of formoterol fumarate dihydrate, each unit dose delivering 9 µg formoterol fumarate dihydrate to the patient; and each daily dose of the second active ingredient, which may be separate from or in admixture with the first active ingredient, is administered as one or more unit doses of budesonide, each unit dose delivering 160 µg of budesonide to the patient.

34. The method of claim 33, wherein the unit doses of both the first active ingredient and the second active ingredient are administered once or twice per day.

35. The method of claim 29, wherein each daily dose of the first active ingredient is administered as one or more unit doses of formoterol fumarate dihydrate, each unit dose delivering 4.5 µg formoterol fumarate dihydrate to the patient; and each daily dose of the second active ingredient, which may be separate from or in admixture with the first active ingredient, is administered as one or more unit doses of budesonide, each unit dose delivering 160 µg of budesonide to the patient.

36. The method of claim 29, wherein the first and second active ingredients are administered together from a single pMDI.

37. The method of claim 29, wherein at least one of the first and second active ingredients is formulated in a propellant comprising one or both of P227 and P134(a).

38. The method of claim 29, wherein the method produces a reduction in frequency or intensity of COPD exacerbations in the patient.

39. The method of claim 29, wherein the method produces an improvement in $FEV_1$ in the patient.

40. A method for treating a patient suffering from COPD, which method comprises administering to the patient, via inhalation from a pMDI, a composition comprising (i) a first active ingredient that is formoterol, a pharmaceutically acceptable salt or solvate thereof, or a solvate of such a salt; (ii) a second active ingredient that is budesonide; and (iii) propellant P227, wherein the molar ratio of (a) formoterol in the first active ingredient to (b) the second active ingredient is from 1:70 to 1:4.

41. The method of claim 40, wherein the patient inhales 4.5 or 9.0 µg formoterol fumarate dihydrate once or twice per day and 80 or 160 µg budesonide once or twice per day.

42. The method of claim 40, wherein the method produces a reduction in frequency or intensity of COPD exacerbations in the patient.

43. The method of claim 40, wherein the method produces an improvement in $FEV_1$ in the patient.

44. A method for the treatment of a patient suffering from COPD, which method comprises administering formoterol fumarate dihydrate and budesonide to the patient via inhalation, wherein the formoterol fumarate dihydrate and budesonide are administered simultaneously and optionally in admixture; the amount of formoterol fumarate dihydrate inhaled by the patient is 18 µg per day; and the amount of budesonide inhaled by the patient is 640 µg per day.

45. A method for the treatment of a patient suffering from COPD, which method comprises administering to the patient via inhalation (i) a daily dose of a first active ingredient that is formoterol, a pharmaceutically acceptable salt or solvate thereof, or a solvate of such a salt, the daily dose of the first active ingredient delivering an amount of formoterol to the patient per day that is equivalent to the amount delivered when 18 µg of formoterol fumarate dihydrate per day is delivered to the patient; and (ii) a daily dose of a second active ingredient that is budesonide, the daily dose of the second active ingredient delivering 640 µg of budesonide to the patient per day, wherein the first active ingredient is optionally in admixture with the second active ingredient, and the two active ingredients are administered simultaneously.

46. A method for the treatment of a patient suffering from COPD, which method comprises administering formoterol fumarate dihydrate and budesonide to the patient via inhalation, wherein the formoterol fumarate dihydrate and budesonide are administered simultaneously, and optionally in admixture, in one to four unit doses per day; the amount of formoterol fumarate dihydrate delivered to the patient by each unit dose of formoterol fumarate dihydrate is 4.5 µg; and the amount of budesonide delivered to the patient by each unit dose of budesonide is 160 µg.

47. The method according to claim 40, wherein the patient inhales 4.5 µg of formoterol fumarate dihydrate and 160 µg of budesonide as a unit dose one to four times per day.

48. The method according to claim 40, wherein the composition further comprises one or more other excipients.

49. The method according to claim 47, wherein the composition further comprises one or more other excipients.

50. The method according to claim 48, wherein the one or more other excipients is selected from ethanol, a lubricant, an antioxidant, and a stabilizing agent.

51. The method according to claim 49, wherein the one or more other excipients is selected from ethanol, a lubricant, an antioxidant, and a stabilizing agent.

52. The method according to claim 47, wherein the formoterol fumarate dihydrate and budesonide are in the form of micronized particles.

53. The method according to claim 44, wherein the formoterol fumarate dihydrate and the budesonide are in admixture and are formulated in a composition comprising a propellant.

54. The method according to claim 45, wherein the formoterol fumarate dihydrate and the budesonide are in admixture and are formulated in a composition comprising a propellant.

55. The method according to claim 46, wherein the formoterol fumarate dihydrate and the budesonide are in admixture and are formulated in a composition comprising a propellant.

56. The method according to claim 53, wherein the propellant comprises one or both of P227 and P134(a).

57. The method according to claim 54 wherein the propellant comprises one or both of P227 and P134(a).

58. The method according to claim 55, wherein the propellant comprises one or both of P227 and P134(a).

59. The method according to claim 53, wherein the composition further comprises one or more other excipients.

60. The method according to claim 54, wherein the composition further comprises one or more other excipients.

61. The method according to claim 55, wherein the composition further comprises one or more other excipients.

62. The method according to claim 59, wherein the one or more other excipients is selected from ethanol, a lubricant, an antioxidant, and a stabilizing agent.

63. The method according to claim 60, wherein the one or more other excipients is selected from ethanol, a lubricant, an antioxidant, and a stabilizing agent.

64. The method according to claim 61, wherein the one or more other excipients is selected from ethanol, a lubricant, an antioxidant, and a stabilizing agent.

65. The method according to claim 53, wherein the formoterol fumarate dihydrate and budesonide are in the form of micronized particles.

66. The method according to claim 54, wherein the formoterol fumarate dihydrate and budesonide are in the form of micronized particles.

67. The method according to claim 55, wherein the formoterol fumarate dihydrate and budesonide are in the form of micronized particles.

68. The method according to claim 53, wherein the formoterol fumarate dihydrate and the budesonide are administered together from a single pMDI.

69. The method according to claim 54, wherein the formoterol fumarate dihydrate and the budesonide are administered together from a single pMDI.

70. The method according to claim 55, wherein the formoterol fumarate dihydrate and the budesonide are administered together from a single pMDI.

71. The method according to claim 44, wherein the formoterol fumarate dihydrate and the budesonide are in admixture.

72. The method according to claim 45, wherein the formoterol fumarate dihydrate and the budesonide are in admixture.

73. The method according to claim 46, wherein the formoterol fumarate dihydrate and the budesonide are in admixture.

74. The method according to claim 71, wherein the formoterol fumarate dihydrate and the budesonide are in the form of a dry powder.

75. The method according to claim 72, wherein the formoterol fumarate dihydrate and the budesonide are in the form of a dry powder.

76. The method according to claim 73, wherein the formoterol fumarate dihydrate and the budesonide are in the form of a dry powder.

77. The method according to claim 71, wherein the formoterol fumarate dihydrate and the budesonide are in the form of an agglomerated, micronized dry powder.

78. The method according to claim 72, wherein the formoterol fumarate dihydrate and the budesonide are in the form of an agglomerated, micronized dry powder.

79. The method according to claim 73, wherein the formoterol fumarate dihydrate and the budesonide are in the form of an agglomerated, micronized dry powder.

80. The method according to claim 71, wherein the formoterol fumarate dihydrate and the budesonide are in the form of an ordered mixture with a pharmaceutically acceptable additive, diluent or carrier.

81. The method according to claim 72, wherein the formoterol fumarate dihydrate and the budesonide are in the form of an ordered mixture with a pharmaceutically acceptable additive, diluent or carrier.

82. The method according to claim 73, wherein the formoterol fumarate dihydrate and the budesonide are in the form of an ordered mixture with a pharmaceutically acceptable additive, diluent or carrier.

83. The method according to claim 71, wherein the formoterol fumarate dihydrate and the budesonide are administered to the patient from a dry powder inhaler.

84. The method according to claim 72, wherein the formoterol fumarate dihydrate and the budesonide are administered to the patient from a dry powder inhaler.

85. The method according to claim 73, wherein the formoterol fumarate dihydrate and the budesonide are administered to the patient from a dry powder inhaler.

\* \* \* \* \*

UNITED STATES PATENT AND TRADEMARK OFFICE
CERTIFICATE OF CORRECTION

PATENT NO. : 7,897,646 B2
APPLICATION NO. : 10/010283
DATED : March 1, 2011
INVENTOR(S) : Carl-Axel Bauer et al.

It is certified that error appears in the above-identified patent and that said Letters Patent is hereby corrected as shown below:

Title Page, Column 2, Other Publications, line 2:

Delete "obsructive" and insert --obstructive--

Title Page, Column 2, Other Publications, line 7:

Delete "Medicine" and insert --Medical--

Title Page, Column 2, Other Publications, line 29:

Delete "Cortiscoteroid" and insert --Corticosteroid--

Title Page, Column 2, Other Publications, line 34:

Delete "117:332D-335S" and insert --117:332S-335S--

Title Page, Column 2, Other Publications, lines 39-41:

Delete "*Compendium Suisse des Medicaments*, 15 th Ed. 1997/1998, Ed. Grand Public, compiled Jun. 1996, pp. 2-3, 419-420,866 (in French)."

and insert two entries:

--*Compendium Suisse des Medicaments*, 15th Ed. 1997/1998, Ed. Grand Public, compiled Jun. 1996, pp. 2-3, 419-420, 866 (in French)
*Compendium Suisse des Medicaments*, 18th Ed. 1997, compiled June 1996, pages 5, 849-851 and 1635-1636 (in French)--

Signed and Sealed this
Twenty-seventh Day of September, 2011

David J. Kappos
*Director of the United States Patent and Trademark Office*